United States Patent
Kwak et al.

(10) Patent No.: US 8,865,074 B2
(45) Date of Patent: Oct. 21, 2014

(54) SAMPLE ANALYSIS CARTRIDGE AND SAMPLE ANALYSIS CARTRIDGE READER

(75) Inventors: Keumcheol Kwak, Seoul (KR); Seokjung Hyun, Seoul (KR); Taeyoon Lee, Seoul (KR); Jitae Kim, Seoul (KR); Dayeon Kang, Seoul (KR); Gueisam Lim, Seoul (KR); Yeonjae Kang, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 13/520,477

(22) PCT Filed: Dec. 29, 2010

(86) PCT No.: PCT/KR2010/009489
§ 371 (c)(1),
(2), (4) Date: Jul. 3, 2012

(87) PCT Pub. No.: WO2011/081437
PCT Pub. Date: Jul. 7, 2011

(65) Prior Publication Data
US 2012/0329144 A1 Dec. 27, 2012

(30) Foreign Application Priority Data
Jan. 4, 2010 (KR) .................. 10-2010-0000227

(51) Int. Cl.
G01N 33/00 (2006.01)
G01N 35/10 (2006.01)
G01N 33/49 (2006.01)
G01N 21/77 (2006.01)
G01N 33/86 (2006.01)
G01N 30/96 (2006.01)
B01L 3/00 (2006.01)
G01N 21/03 (2006.01)

(52) U.S. Cl.
CPC ....... *G01N 33/4915* (2013.01); *B01L 2200/143* (2013.01); *G01N 2021/0346* (2013.01); *G01N 35/1095* (2013.01); *B01L 3/502746* (2013.01); *G01N 33/4905* (2013.01); *B01L 2300/0645* (2013.01); *G01N 21/77* (2013.01); *G01N 33/86* (2013.01); *B01L 2300/0864* (2013.01); *B01L 2400/0406* (2013.01)
USPC ............... 422/73; 422/69; 422/502; 422/503; 422/507; 422/534; 422/535; 422/551

(58) Field of Classification Search
CPC ............... G01N 33/86; G01N 33/4905; B01L 2400/0406
See application file for complete search history.

(56) References Cited

U.S. PATENT DOCUMENTS

| | | | |
|---|---|---|---|
| 7,857,761 B2 * | 12/2010 | Lee et al. | 600/368 |
| 2004/0018629 A1 * | 1/2004 | Kawate | 436/63 |
| 2005/0130292 A1 | 6/2005 | Ahn et al. | |
| 2005/0210962 A1 | 9/2005 | Bohm et al. | |
| 2005/0269251 A1 | 12/2005 | Cork et al. | |
| 2008/0297169 A1 * | 12/2008 | Greenquist et al. | 324/600 |
| 2009/0269837 A1 | 10/2009 | Shevkoplyas et al. | |

FOREIGN PATENT DOCUMENTS

JP 2008-203234 A 9/2008

* cited by examiner

*Primary Examiner* — Jill Warden
*Assistant Examiner* — Brittany Fisher
(74) *Attorney, Agent, or Firm* — Birch, Stewart, Kolasch & Birch, LLP

(57) ABSTRACT

A sample analysis cartridge and a sample cartridge reader are provided. In measuring a particular component included in a sample flowing in a microfluidic channel, a numerical value of hematocrit is reflected to thus improve the accuracy of measurement of the particular component.

10 Claims, 5 Drawing Sheets

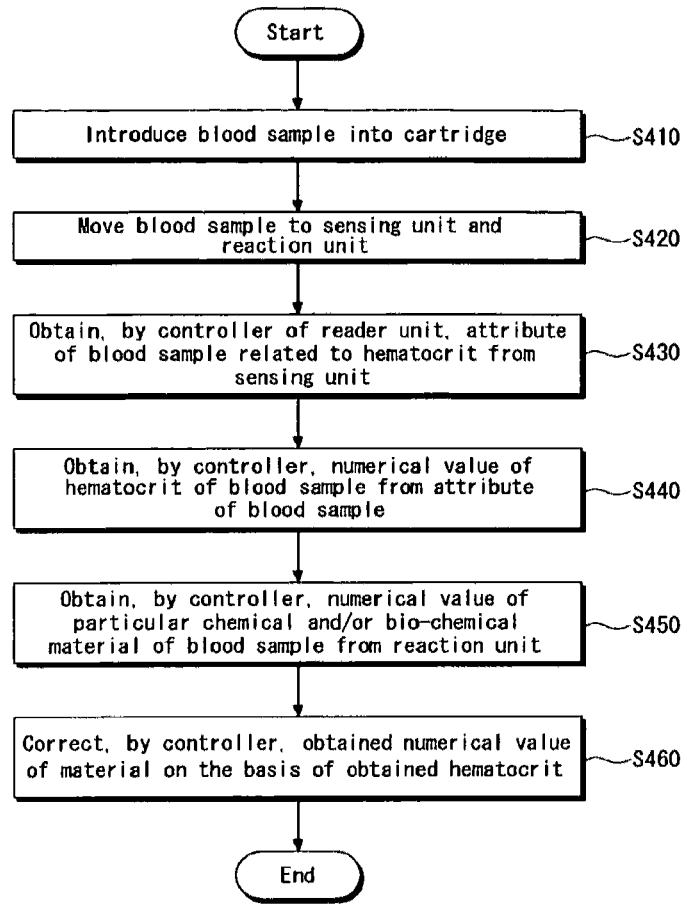
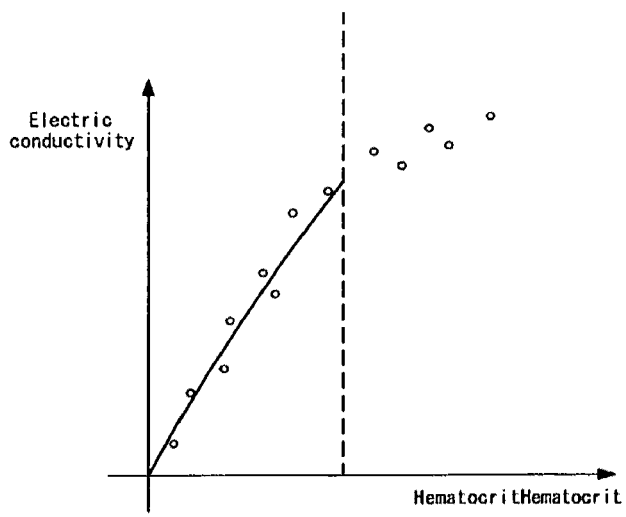

| Hematocrit | Electric conductivity | Light transmittance | Contact angle | Viscosity coefficient | Speed |
|---|---|---|---|---|---|
| a1 | b1 | c1 | d1 | e1 | f1 |
| a2 | b2 | c2 | d2 | e2 | f2 |
| a3 | b3 | c3 | d3 | e3 | f3 |

SAMPLE ANALYSIS CARTRIDGE AND SAMPLE ANALYSIS CARTRIDGE READER

TECHNICAL FIELD

The present invention relates to a sample analysis cartridge and a cartridge reader for measuring a chemical and/or biochemical material in a blood sample by using a microfluidic channel and, more particularly, to a cartridge and a reader capable of accurately measuring a numerical value of a chemical and/or bio-chemical material in a blood sample by correcting an error according to hematocrit.

BACKGROUND ART

A method of collecting a patient's body fluids or blood and checking chemical or bio-chemical materials related to a disease in a central laboratory has been generalized.

Recently, a method for allowing a doctor, a nurse, a clinical laboratory technologist in the presence of a patient, or the patient himself, to do a checkup with respect to a disease cause, and demand for an artificial intelligence type small measurement device doing such a checkup and automatically transmitting the results to a central patient management system is rapidly increasing.

Thus, research for point-of-care testing (POCT) capable of quickly and accurately providing a checkup required for patients through an on-the-spot measurement, moving away from a central checkup laboratory incurring much time and cost, is being actively ongoing in universities, institutes, or large enterprises.

DISCLOSURE OF INVENTION

Technical Problem

An aspect of the present invention provides a sample analysis cartridge and a cartridge reader capable of measuring a numerical value of a chemical and/or bio-chemical material in a blood sample by reflecting a numerical value of hematocrit to thus improve the accuracy of measurement of the numerical value of the chemical and/or bio-chemical material.

Solution to Problem

According to an aspect of the present invention, there is provided a sample analysis cartridge including: an inlet through which a blood sample is introduced; a microfluidic channel connected to the inlet and providing a movement path of the blood sample; and a sensing unit positioned in the microfluidic channel and sensing an attribute of the blood sample to obtain hematocrit of the blood sample.

According to another aspect of the present invention, there is provided a sample analysis cartridge reader including: a controller configured to obtain hematocrit from the attribute of a blood sample sensed in a cartridge.

According to exemplary embodiments of the present invention, in the cartridge and the cartridge reader, the numerical value of a particular chemical and/or bio-chemical material in a blood sample and a hematocrit value are obtained and the numerical value according to hematocrit are corrected to thus improve accuracy of the measurement.

Advantageous Effects of Invention

The present invention the present invention the present invention the present invention

BRIEF DESCRIPTION OF DRAWINGS

FIG. 4 is a flow chart illustrating the process of a method for correcting a measured cholesterol numerical value on the basis of hematocrit according to an exemplary embodiment of the present invention;

FIG. 5 is a graph showing the relationship between electric conductivity and hematocrit;

BEST MODE FOR CARRYING OUT THE INVENTION

Figure 1:
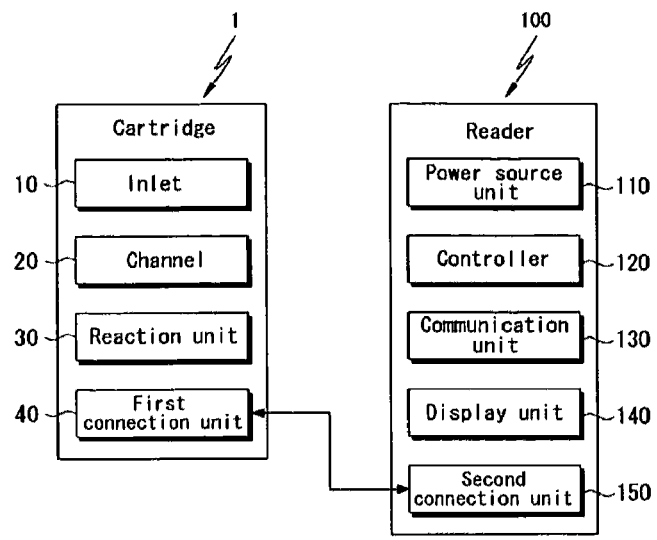
FIG. 1 is a schematic block diagram of a cartridge and a reader according to an exemplary embodiment of the present invention.

Exemplary embodiments of the present invention will now be described in detail with reference to the accompanying drawings.

Like reference numerals are used for like elements of the drawings and a repeated description of like elements may be omitted.

Terms used in the present disclosure are merely used for explaining a particular embodiment and the scope of the present invention is not limited thereto.

FIG. 1 is a schematic block diagram of a cartridge and a reader according to an exemplary embodiment of the present invention.

The cartridge 1 may include an inlet 10, a channel 20, a reaction unit 30, and a first connection unit 40.

The cartridge 1 may generate a certain signal corresponding to a numerical value of a particular chemical and/or bio-chemical material included in a blood sample introduced into the cartridge 1. For example, the cartridge 1 may generate a recognizable signal such as a color, phosphor, or electrical signal corresponding to the numerical value of the material.

Hereinafter, a sample refers to the blood sample.

The inlet 10 may correspond to an entrance of the channel 20. The inlet 10, serving to receive the blood sample, may have a certain cross section to facilitate the introduction of the blood sample.

The inlet 10 may communicate with the channel 20. Namely, the blood sample introduced to the inlet 10 may flow in and along the channel 20.

The channel 20 may be connected to the inlet 10. The channel 20 may provide a movement path allowing the sample introduced to the inlet 10 to pass therethrough. The channel 2 may be provided to allow the blood sample to move to the reaction unit 30 in which the blood sample is processed and reacted.

The blood sample may move by using a capillary force, pressure, a centrifugal force as power within the channel 20.

The channel 20 may be, for example, a microfluidic channel. The microfluidic channel may refer to a channel in which the sample may move or flow according to a capillary action.

The reaction unit 30 is connected to the channel 20. The sample may be introduced into the reaction unit through the channel 20.

The reaction unit 30 may generate a certain signal that changes according to the numerical value of a particular chemical and/or bio-chemical material included in the sample. The certain signal may include color and/or electrical signal.

The reaction unit 30 may process the sample in order to generate the certain signal. The processing may be performed by a substrate, a catalyst, enzyme, or the like.

The reaction unit 30 may generate a color and/or electrical signal by using an optical or electrochemical method in order to measure the numerical value of the particular chemical and/or bio-chemical material included in the processed sample.

The optical and/or electrochemical method will be described as follows.

The optical method refers to a method of using optical characteristics of the processed sample. The optical method may include colorimetry, i.e., an analysis method for quantifying a color tune of sample liquid by comparing it with a color tune of a standard solution (or a standard liquor), a fluorescence method for measuring unique light emitted when a certain type of material receives light, an electron beam, X-ray, or radiation, and a chemiluminescence method for measuring light generated as a result of a chemical reaction.

The electrochemical method uses electrical characteristics of the processed sample. For example, the electrochemical method may include a generation of current and/or voltage from the processed sample.

Various types of chemical and/or bio-chemical materials may be measured from the reaction unit 30. For example, the chemical and/or bio-chemical materials may include sugar, cholesterol, and the like.

The first connection unit 40 may be connected to a second connection unit 150 of a reader 100. The first connection unit 40 serves to transmit the color and/or electrical signal generated by the cartridge 1 to the reader 100. Also, the first connection unit 40 may transmit the signal generated from the cartridge 1 to the reader 100 or receive a required signal from the reader 100.

The reader 100 connected to the cartridge 1 will now be described in detail.

The reader 100 may serve to process a signal generated by the cartridge 1.

The reader 100 may include a power source unit 110, a controller 120, a communication unit 130, a display unit 140, and a second connection unit 150.

The power source unit 110 may provide required power to the cartridge 1 and/or the reader 100.

The controller 120 may control the respective elements of the reader 100.

The communication unit 130 may transmit medical information to a different medical device or receive required information therefrom.

The display unit 140 may display the measured numerical value of the chemical and/or bio-chemical material to allow the user to view it.

The second connection unit 150 may be connected to the first connection unit 40 of the cartridge 1 and receive a color and/or electrical signal from the first connection unit 40.

Figure 2:
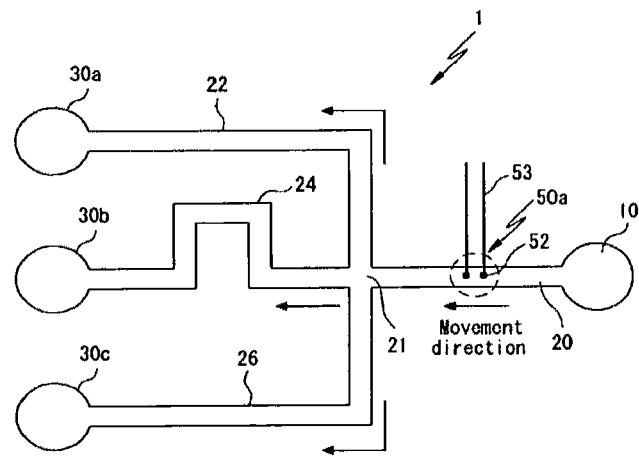
FIG. 2 is a perspective view of the cartridge according to an exemplary embodiment of the present invention.

FIG. 2 is a perspective view of the cartridge according to an exemplary embodiment of the present invention.

With reference to FIG. 2, the cartridge 1 may include the inlet 10, a plurality of channels 20, 22, 24, and 26, a plurality of reaction units 30a, 30b, and 30c, and a sensing unit 50a. A description of the same elements as those illustrated in FIG. 1 will be omitted.

The panel 20 may be branched into child channels 22, 24, and 26 from a branch point 21.

The channels are configured to allow the blood sample having the same volume per unit time to simultaneously reach the reaction units 30a, 30b, and 30c. To this end, the channels 22, 24, and 26 are configured to have the same width, so that the same volume of blood sample per unit time can reach the reaction units 30a, 30b, and 30c. In this case, in particular, the channel 24 includes a curved portion formed to be bent to make the length of the path reaching the channel 24 and the reaction unit 30b equal to the length of the paths reaching the channels 22 and 26 and the reaction units 30a and 30c. Accordingly, the blood sample can simultaneously reach the reaction units 30a, 30b, and 30c.

The reaction units 30a, 30b, and 30c may be positioned at respective ends of the channels 22, 24, and 26.

The reaction units 30a, 30b, and 30c may be an example of the reaction unit 30 described above with reference to FIG. 1, providing the same function as that of the reaction unit 30.

The reaction unit 30 may generate a color and/or electrical signal related to a particular chemical and/or bio-chemical material included in the blood sample as discussed above.

Hereinafter, the particular chemical and/or bio-chemical material is assumed to be cholesterol.

Cholesterol, one of lipid constituting cell membrane of an animal cell, may circulate along the bloodstream in a body.

Because cholesterol is fat, not dissolved in blood, so it forms a complex with lipoproteins. Lipoproteins are divided into very low-density lipoproteins (VLDL), low-density lipoproteins (LDL), high-density lipoproteins (HDL), and triglyceride according to the density of lipoproteins.

The reaction units 30a, 30b, and 30c may generate a color and/or electric signal related to total cholesterol, HDL, and triglyceride, respectively.

The reaction units 30a, 30b, and 30c may include a substrate or a catalyst for a pre-processing procedure for generating a color and/or signal. The catalyst may include enzyme.

For example, in order to measure total cholesterol, the reaction units 30a, 30b, and 30c may use cholesterol esterase (CE), cholesterol oxidase (COD), and per oxidase (POD) as enzymes.

In order to measure the HDL, the reaction units 30a, 30b, and 30c may use PEG-CE (polyethylene glycol-modified cholesterol esterase), COD, and POD as enzymes.

In order to measure the triglyceride, the reaction units 30a, 30b, and 30c may use lipase, glycerol kinase, GPO (Glycerol-3-Phosphate Oxidase), and POD as enzymes.

In order to measure a particular chemical and/or bio-chemical material from the processed blood sample, for example, in order to measure how much cholesterol is contained in the blood sample, the reaction units 30a, 30b, and 30c use the optical method and/or the electrochemical method.

In the following exemplary embodiment, it is assumed that the electrochemical method is used.

In order to measure a numerical value of cholesterol through the electrochemical method, the reaction units 30a, 30b, and 30c may further include a light emitting element and a light receiving element. For example, the light emitting element and the light receiving element may be configured as a light emitting diode (LED) and a photo diode (PD), respectively.

The light emitting element of each of the reaction units 30a, 30b, and 30c may irradiate light to the processed blood sample.

The irradiated light may be partially diffused by the material included in the processed blood sample, partially absorbed, and remaining light may be concentrated to the light receiving element.

Namely, the intensity of light concentrated to the light receiving element may vary depending on the amount of cholesterol contained in the processed blood sample.

Thus, the reaction units 30a, 30b, and 30c may generate an electrical signal varying depending on the amount of cholesterol contained in the processed blood sample, respectively.

To sum up, the reaction units 30a, 30b, and 30c process the blood sample reaching through the respective channels 22, 24, and 26 with the substrate and enzymes, generate an electrical signal from the processed blood sample by using the electro-chemical method, thus generating the signal corresponding to the numerical value of cholesterol.

However, the numerical value of cholesterol measured in this manner may not be accurate. The reason is because, even when the volume of the blood sample reaching the reaction units 30a, 30b, and 30c per unit time is equal, there is an error with respect to light concentrated to the light receiving element due to various interference materials such as hematocrit, or the like.

Here, hematocrit is defined as the ratio of volume of a solid component such as a red blood cell component, or the like, to the entire blood.

The value of hematocrit significantly changes to be 20% to 60% according to people and may cause an interference phenomenon when a particular component within blood is measured.

For example, it is assumed that numerical values of cholesterol of blood samples A and B per 10 ml are measured to be 5 and 5 and their hematocrits are 20 and 60 respectively. In this case, although the absolute cholesterol numerical values are equal, because hematocrit of the blood sample B is higher than that of the blood sample A, the density of cholesterol of the blood sample B is considered to be higher.

In other words, hematocrit varies to range from 20% to 60% depending on people, so although the blood samples having the same volume per unit time simultaneously reach the reaction units 30a, 30b, and 30c, the actual volumes of blood plasma (serum) in which cholesterol can be included may differ.

Thus, in order to correct the error due to the difference in the hematocrit, the cartridge 1 may further include a sensing unit 50.

The sensing unit 50 may be provided to sense the attributes of the blood sample related to hematocrit.

The attributes of the blood sample may include electric conductivity of the blood sample, light transmittance of the blood sample, a contact angle between the blood sample and an inner wall of the microfluidic channel, a viscosity coefficient, a movement speed, and the like. Here, sub-attributes of the blood sample for measuring the viscosity coefficient may include flux of the blood sample per second, a pressure difference between two points, and the like, and sub-attributes of the blood sample for measuring the movement speed may include the distance between certain two points within the microfluidic channel, a duration in which the blood sample passes through two certain points in the microfluidic channel, and the like.

The sensing unit 50a illustrated in FIG. 2 may be an example of the sensing unit 50, which is able to sense electric conductivity of the blood sample.

When electric conductivity is high, hematocrit is relatively high, and when electric conductivity is low, hematocrit is relatively low. Thus, hematocrit can be obtained by using such relationships.

The sensing unit 50a using the relationships will now be described.

The sensing unit 50a may be positioned between the branch point 21 of the channel and the inlet 10. The position of the sensing unit 50a is merely an example and the sensing unit 50a may be placed at any position where it can measure electric conductivity of the blood sample. Positioning of the sensing unit 50a between the branch point 21 and the inlet 10 can provide an effect of making the blood sample having the same volume per unit time simultaneously reach the plurality of reaction units.

The sensing unit 50a, serving to measure electric conductivity of the sample, one of the attributes of the blood sample for measuring hematocrit, may include two electrodes 52 and electric wires 53 connected to the two electrodes 52.

Electric conductivity may be defined to be a measure of a material's or solution s ability to conduct an electric current. In this case, the measure of conducting an electric current of the sample is proportional to hematocrit, so hematocrit can be known or recognized by measuring the strength of current.

To this end, the pair of electrodes 52 may be positioned in the channel 20.

The pair of electrodes 52 may be positioned to face each other or in parallel.

The electrodes 52 may be made of gold, carbon, silver, or platinum.

Any other materials of the electrodes may be those not reacted to blood because the sample is blood.

The electrodes 52 may be connected to the power source unit 110 through the electric wires 53. Namely, the power source unit 110 may supply a certain voltage to the electrodes 52 of the cartridge 1.

Through such a configuration, hematocrit and cholesterol included in the blood sample can be measured once and the numerical value of cholesterol can be corrected according to hematocrit, thus obtaining an accurate numerical value of cholesterol.

Figure 3:
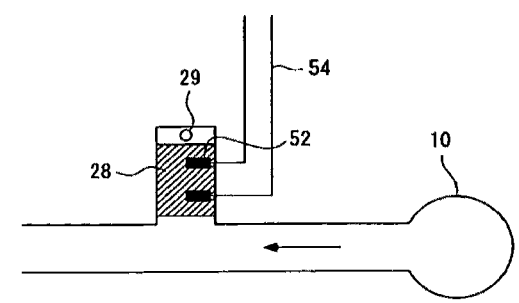
FIG. 3 is a view for explaining another example of the electrical conductivity sensing unit according to an exemplary embodiment of the present invention.

FIG. 3 is a view for explaining another example of the electrical conductivity sensing unit according to an exemplary embodiment of the present invention.

The sensing unit 50a may include electrodes 52 and electric wires 54.

The sensing unit 50a according to the present exemplary embodiment illustrated in FIG. 3 is different from that according to the former exemplary embodiment illustrated in FIG. 2 in that the structures of the channels 20 are different.

The channel 20 may include a projection 28 at a certain portion thereof. A vent 29 may be positioned on the projection 28.

The operation method of the electric conductivity sensing unit 50a will be described as follows.

When the blood sample is introduced into the inlet 10, the blood sample is bound to move along the channel 20.

While the blood sample is moving along the channel 20, a portion thereof is introduced into the projection and the other remaining portions may proceed toward the branch point 21.

In this case, the vent 29 allow air to be well released from the interior of the projection 28, thus helping the sample, which flows in and through the channel 20, be introduced into the projection 28.

After the blood sample moves to the reaction units 30a, 30b, and 30c.the portion of the sample which has been introduced into the projection 28 remains as it is in the interior of the projection 28 due to a viscose force between the sample and the inner wall of the projection 28. Namely, the introduced blood sample is divided into the blood sample which has reached the reaction units 30a, 30b, and 30c and the blood sample remaining in the projection 28.

Preferably, the width of the projection 28 is formed to be narrow in order to increase the viscosity force with the sample.

With the blood sample remaining in the interior of the projection 28, when a certain voltage is applied through the electrodes 52, electric conductivity of only the sample having a certain volume and remaining in the projection 28 can be measured.

Although the amount of sample introduced into the inlet 10 is different, the volume of the blood sample remaining in the projection 28 is uniform, so the accuracy of measuring the electric conductivity can be improved.

In addition, a detection unit (not shown) may be further included.

The detection unit may generate a signal for determining when to apply voltage to the electrodes 52 and transmit the generated signal to the controller 120 through the first and second connection units 40 and 150.

For example, in a state in which the blood sample is introduced into the projection 28, a time when the blood sample introduced into the projection 28 is separated from the blood sample which moves to the reaction units may be considered as a voltage application time point.

To this end, the detection unit may be positioned between the projection 28 and the branch point 21.

Namely, the flow of the blood sample between the projection 28 and the branch point 21 is detected, and thereafter, when no flow of blood sample is detected, the voltage application time point may be transmitted to the controller 120.

The detection unit, may be configured, for example, as a light emitting element or a light receiving element, or may be configured as an electrode.

Figures 6, 7:
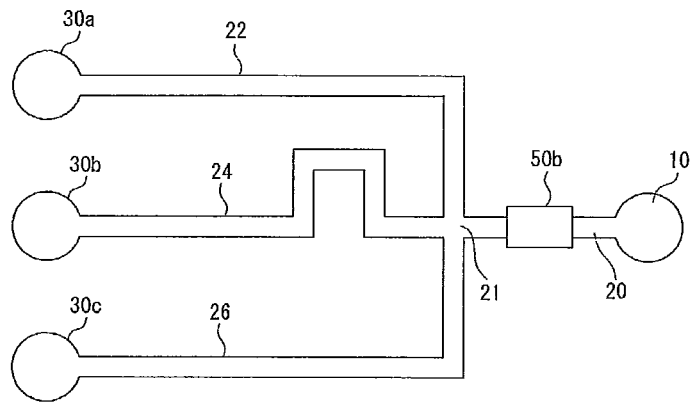
FIG. 6 is a table showing the relationship between attributes of blood samples related to hematocrit and the hematocrit.
FIG. 7 is a perspective view of a cartridge according to another exemplary embodiment of the present invention.

FIG. 4 is a flow chart illustrating the process of a method for correcting a measured cholesterol numerical value on the basis of hematocrit according to an exemplary embodiment of the present invention. FIG. 5 is a graph showing the relationship between electric conductivity and hematocrit. FIG. 6 is a table showing the relationship between attributes of blood samples related to hematocrit and the hematocrit.

The operation method using the structure of the cartridge 1 and the reader 100 illustrated in FIGS. 1 and 3 will now be described in detail.

In the below description, steps S410 and S420 are performed in the cartridge 1, and the follow-up steps are performed in the reader 100.

The blood sample may be introduced into the cartridge (S410). Namely, the inlet 10 may receive the blood sample.

The blood sample may move to the sensing unit and the reaction units along the channel (S420).

The sample may flow in and along the channel 20 according to capillary action. Namely, the sample may pass through the sensing unit 50 and the reaction unit 30.

The sensing unit 50 may sense the attributes of the blood sample related to hematocrit of the blood sample. Also, the reaction unit 30 may generate a color and/or electrical signal corresponding to a numerical value of a particular chemical and/or bio-chemical material, e.g., cholesterol, included in the blood sample.

The cartridge 1 may be connected to the reader 100 at a certain point in time when steps S410 and S420 are performed or after step S420 is completed.

The controller 120 of the reader 100 may obtain the attribute of the blood sample related to hematocrit included in the blood sample from the sensing unit 50 (S430).

Namely, when a voltage application signal generated by the detection unit is received through the first connection unit 40 and the second connection unit 150, the controller 120 may apply voltage to the electrode 52 of the sensing unit 50a.

By supplying the voltage to the sensing unit 50a, the controller 120 may be able to obtain a numerical value of electric conductivity of the blood sample, one of the attributes of the blood sample.

The controller 120 can obtain electric conductivity on the basis of the strength of current at the sensing unit 50a.

Because the controller 120 already knows about the strength of the voltage applied to the electrode 52, it can know about the resistance of the sample on the basis of the strengths of the current and voltage and obtain the electric conductivity, a reciprocal number of the resistance.

The controller 120 can obtain a numerical value of hematocrit of the blood sample from the attributes of the blood sample (S440).

The relationship between the electric conductivity, one of the attributes of the blood sample, and hematocrit is show in FIG. 5. Namely, because the electric conductivity is correlated with hematocrit, a function can be obtained on the basis of the correlation. Or, the controller 120 can obtain a particular numerical value of hematocrit corresponding to a particular electric conductivity from a standard solution table illustrated in FIG. 6.

The standard solution table of FIG. 6 will now be described to help understand.

The standard solution refers to a solution having an accurate concentration of a material desired to be measured.

Namely, in a state in which the user knows about hematocrit through experimentation, the user can obtain electric conductivity, a light transmittance, a contact angle, a viscosity coefficient, and speed at the corresponding hematocrit, forms a table with these factors, and store the same in the reader 100 or provide the same through the communication unit 130.

As shown in FIG. 6, the controller 120 can recognize that hematocrit is a1 when electric conductivity measured by the sensing unit 50a is b1, and hematocrit is a2 and a3 when electric conductivity is b2 and b3, respectively.

The controller 120 can obtain a numerical value of a particular chemical and/or bio-chemical material of the blood sample from the reaction unit 30 (S450).

As mentioned above, the material may be cholesterol.

The reaction unit 30 may generate a color and/or electrical signal corresponding to the numerical value of cholesterol.

The controller 120 may receive the color and/or electrical signal from the reaction unit 30 through the first connection unit 40 and the second connection unit 150.

For example, when the reaction unit 30 uses an electrochemical method, the controller 120 may obtain a numerical value of cholesterol from a current strength on the basis of the intensity of light concentrated to the photo diode.

Namely, the controller 120 can obtain the numerical value of cholesterol of the introduced blood sample, namely, numerical values of total cholesterol, HDL, and triglyceride.

The controller 120 can correct the cholesterol value on the basis of the obtained hematocrit (S460).

As described above, hematocrit included in a blood sample of each person differs, and the different hematocrit may work as an error in measuring cholesterol. Thus, the numerical value of cholesterol measured on the basis of hematocrit needs to be corrected.

To this end, the controller 120 may correct the cholesterol value measured on the basis of certain hematocrit.

Namely, the hematocrit may be normalized by, for example, 40%, and the numerical value of cholesterol may be corrected on the basis of the 40% of hematocrit.

Accordingly, the numerical value of cholesterol can be corrected on the basis of hematocrit.

Also, the controller 120 may transmit the hematocrit and/or the numerical value of cholesterol of the sample to a different device through the communication unit 130.

For example, the controller 120 may transmit the hematocrit and/or the numerical value of cholesterol of the sample to a personal terminal for a medical diagnosis, a medical information processing device, and a medical institution.

The controller 120 may output the hematocrit and/or the cholesterol degree through the display unit 140 so that the user can view them.

The method of correcting hematocrit through the cartridge 1 including the sensing unit for sensing electric conductivity has been described. Hereinafter, additional exemplary embodiments of the sensing unit, which senses hematocrit, for measuring other attributes of the blood sample will now be described.

Figure 8:
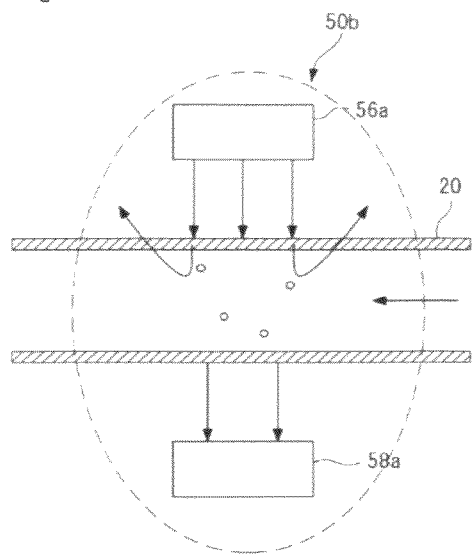
FIG. 8 is a side view of a sensing unit 50b of FIG. 7.

FIG. 7 is a perspective view of a cartridge according to another exemplary embodiment of the present invention. FIG. 8 is a side view of a sensing unit 50b of FIG. 7. The present exemplary embodiment will now be described with reference to FIGS. 7 and 8. The cartridge according to the exemplary embodiment illustrated in FIG. 2 and the cartridge according to the exemplary embodiment illustrated in FIG. 7 are different in the sensing unit, so the sensing unit will be largely described.

FIG. 7 shows a method of using light transmittance as an attribute of a blood sample for sensing hematocrit of a sample.

The relationship between hematocrit of the blood sample and light transmittance of the blood sample is as follows.

When light is irradiated to the blood sample, a portion of the light is disused, a portion of the light is absorbed, and the other remaining light passes through the blood sample. In this case, the size of the portion of the light which is diffused or absorbed is related to a numerical value of hematocrit.

For example, as the numerical value of hematocrit is high, light transmittance is reduced, and as the numerical value of hematocrit is low, the light transmittance is increased.

Thus, when the numerical value of light that passes through the blood sample is known, the numerical value of hematocrit can be recognized.

The sensing unit 50b using such a relationship may be configured to include a light emitting unit 56a and a light receiving unit 58a.

The light emitting unit 56a may be at least one of a light emitting diode, a lamp, and a laser.

The light receiving unit 58a may be a photo diode, a charge coupled device (CCD) array, and a photo diode array.

As shown in FIG. 8, the light emitting unit 56a, the channel 20, and the light receiving unit 58a may be vertically positioned to be parallel to a movement direction of the blood sample.

The light receiving unit 58a may be positioned at the opposite side of the channel 20 in order to receive light irradiated from the light emitting unit 56a. Namely, the light receiving unit 58a and the light emitting unit 56a may be disposed to face each other with the channel 20 interposed therebetween. However, this position relationship may be an example and the scope of the present invention is not limited thereto.

An operation method will now be described.

The light emitting unit 56a of the sensing unit 50b may irradiate light to the blood sample.

In order to know whether or not the blood sample is positioned at the sensing unit 50b, a detection unit (not shown) for detecting whether or not blood sample has passed therethrough may be provided at a portion of the channel 20.

When the amount of transmitted light or the strength of current changes by more than a certain level, the detection unit may transmit a detection signal indicating that the blood sample has passed, to the controller 120.

When the controller 120 receives the detection signal indicating that the blood sample has passed a particular point, it may issue a command for irradiating light to the light emitting unit 56a.

The presence of the light irradiation command means that there is blood sample in the sensing unit 50b, so the light emitting unit 56a irradiates light.

A portion of the irradiated light is reflected by the blood sample, a portion of the light is absorbed, and the other remaining light is concentrated to the light receiving unit 58a.

The light receiving unit 58a may transmit current corresponding to a numerical value of the concentrated light to the controller 120 through the first and second connection units 40 and 150.

Through the foregoing process, the sensing unit 50b can measure the light transmittance of the blood sample and generate an electrical signal for sensing hematocrit of the blood sample.

The operation method according to the exemplary embodiments illustrated In FIGS. 7 and 8 can be described with reference to FIG. 4 as follows. Steps S410 and S420 are the same as described above.

The sensing unit 50b may measure light transmittance of the blood sample, as an attribute of the blood sample related to hematocrit (S430).

The controller 120 can obtain hematocrit from the light transmittance (S440).

For example, the controller can recognize that hematocrit is a1, a2, and a3 when light transmittance is c1, c2, and c3, respectively, with reference to the standard solution table illustrated in FIG. 6.

Steps S450 and S4600 are the same as described above. Through this method, hematocrit can be obtained on the basis of the light transmittance of the blood sample, and a numerical value of cholesterol of the blood sample detected at the reaction unit can be corrected by reflecting the obtained hematocrit.

Figure 9:
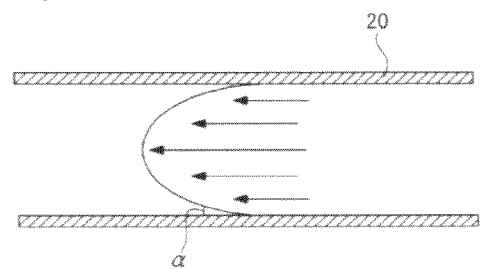
FIGS. 9 and 10 are views showing another example of the sensing unit according to an exemplary embodiment of the present invention.
Figure 10:
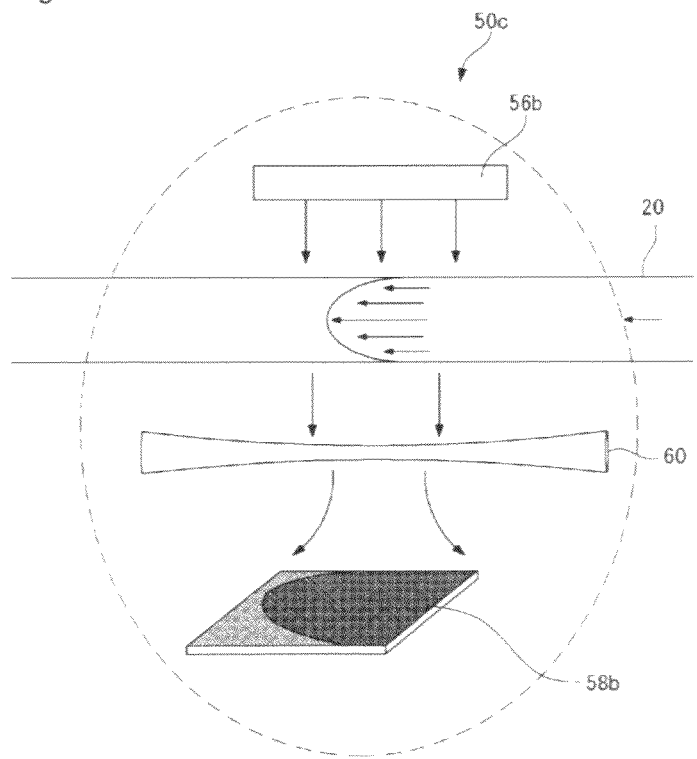

FIGS. 9 and 10 are views showing another example of the sensing unit according to an exemplary embodiment of the present invention.

FIG. 9 shows a contact angle between the sample and an inner wall of the channel when the sample flows along the channel, and FIG. 10 illustrates the light emitting unit 56b and the light receiving unit 58b for measuring the contact angle.

An exemplary embodiment of FIGS. 9 and 10 uses a method of using a contact angle between the sample flowing in the channel and the inner wall of the channel, as an attribute of the blood sample for measuring hematocrit included in the blood sample.

Because the blood sample has a viscosity force, shear force works between the sample and the inner wall of the channel. Owing to the shear force with the inner wall of the channel, the speed of the sample is faster at the central portion of the channel and becomes slower toward the inner wall of the channel. Thus, a certain contact angle may be formed between a stream line of the sample and the inner wall of the channel.

As hematocrit is high, the viscosity increases, so the contact angle may be formed to be relatively small. Also, as hematocrit is low, the viscosity decreases, so the contact angle may be formed to be relatively large.

A numerical value of corresponding hematocrit can be obtained by measuring the contact angle between the blood sample and the inner wall of the channel by using these relationships by the sensing unit 50c.

To this end, the sensing unit 50c may include the light emitting unit 56b and the light receiving unit 58b.

The configuration and function of the light emitting unit 56b are the same as those of the light emitting unit 56a.

The light receiving unit 58b needs to obtain a contact angle on the basis of light irradiated from the light emitting unit 56b, so it may be configured as a CCD array or a photo diode array for measuring the contact angle.

As for the position relationship between the light emitting unit 56b and the light receiving unit 58b, the light emitting unit 56b and the light receiving unit 58b may be positioned such that light irradiated from the light emitting unit 56b passes through the blood sample so as to be concentrated to the light receiving unit 58b.

The contact angle between the blood sample and the inner wall of the channel can be obtained in a following manner.

The light emitting unit 56b may irradiate light to the blood sample.

When a header of the blood sample reaches the sensing unit 50c, the controller 120 may issue a command for irradiating light to the light emitting unit 56b. The controller 120 can determine whether or not the blood sample is positioned at the sensing unit 50c through the foregoing detection unit. In this case, because the contact angle can be measured only at the header of the blood sample, the detection unit may be provided at a position where whether or not the header of the blood sample enters the sensing unit 50c can be determined.

Light irradiated by the light emitting unit 56b proceeds to the header of the blood sample.

The light receiving unit 58b can collect a relatively small amount of light at portions where light is absorbed and diffused by the blood sample and collect a relatively large amount of light at a portion where the there is so blood sample.

Accordingly, the intensity of collected light at the portions of the light receiving unit 58b may vary depending on the shape of the blood sample forming the contact angle.

In order to improve resolution of light collected by the light receiving unit 58b, a concave lens 60 may be positioned between the channel and the light receiving unit 58b. Alternatively, in order to improve the intensity of collected light, a convex lens may be used.

An array piece of the light receiving unit 58b may generate an electrical signal corresponding to the intensity of light, respectively.

The generated electrical signal may be transmitted to the controller 120 through the first and second connection units 40 and 150.

The controller 120 may obtain the contact angle on the basis of the intensity of light collected by the light receiving unit 58b. Accordingly, the contact angle between the sample and the inner wall of the channel can be obtained.

An operation method according to the exemplary embodiment illustrated in FIGS. 9 and 10 will now be described with reference to FIG. 4.

Steps S410 and S420 are the same as those described above.

The controller 120 may obtain the contact angle between the blood sample moving in and along the channel and the inner wall of the channel, as an attribute of the blood sample related to hematocrit from the sensing unit 50c (S430).

Namely, the array piece of the light receiving unit 58b of the sensing unit 50c transmits an electrical signal corresponding to the intensity of the collected light to the controller 120.

The controller 120 can obtain the contact angle on the basis of the strength of the electrical signal.

The controller 120 can obtain hematocrit from the contact angle (S440).

For example, the controller can recognize that hematocrit is a1, a2, and a3 when the contact angle is d1, d2, and d3, respectively, with reference to the standard solution table illustrated in FIG. 6.

Steps S450 and S460 are the same as described above. Through this method, hematocrit can be obtained on the basis of the contact angle between the blood sample and the inner wall of the channel, and a numerical value of cholesterol of the blood sample detected at the reaction unit can be corrected by reflecting the obtained hematocrit.

Figure 11:
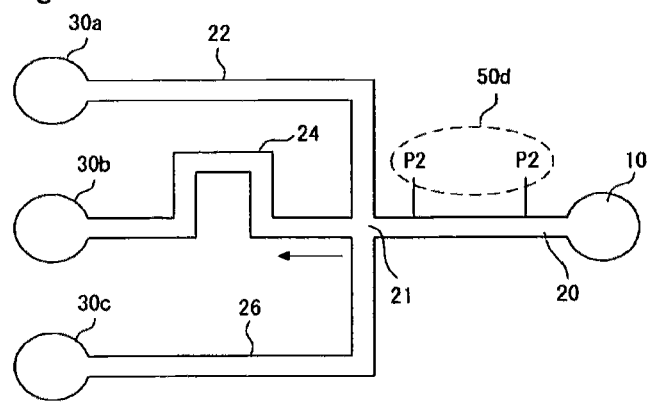
FIG. 11 is a view showing still another example of the sensing unit according to an exemplary embodiment of the present invention.

FIG. 11 is a view showing still another example of the sensing unit according to an exemplary embodiment of the present invention.

An exemplary embodiment of FIG. 11 uses a method of using a movement speed of the blood sample, as an attribute of the blood sample for measuring hematocrit included in the blood sample.

The hematocrit and the movement speed in channel of the blood sample have the following relationship.

As hematocrit is high, the movement speed of the sample decreases, and as hematocrit is low, the movement speed of the sample increases.

Thus, when the movement speed of the blood sample in the channel is known, a numerical value of hematocrit corresponding to the movement speed can be obtained.

In order to implement this, a sensing unit 50d may sense the movement of blood sample when the blood sample passes through certain two points.

Namely, the sensing unit 50d may be configured as a detection unit for detecting the movement of the blood sample when the blood sample passes through the points P1 and P2.

The detection unit may be configured as an electrode for detecting the movement of the blood sample as stated above, or may be configured as a sensor for detecting a change in light transmittance by the blood sample.

The detection unit placed at the position P1 may transmit a signal to the controller 120 when the blood sample passes through P1.

The detection unit placed at the position P2 may transmit a signal to the controller 120 when the blood sample passes through P2.

The controller 120 may obtain a passage duration on the basis of the time at which the blood time passes through the points P1 and P2, respectively.

Also, the controller 120 may know about the distance between the points P1 and P2 by previously storing them or upon receiving information regarding the distance from the cartridge 1.

Accordingly, the controller 120 can obtain the movement speed of the blood sample through the sensing unit 50d.

An operation method according to the exemplary embodiment illustrated in FIG. 11 will now be described with reference to FIG. 4.

Steps S410 and S420 are the same as those described above.

The controller 120 may obtain the movement speed of the blood sample, as an attribute of the blood sample related to hematocrit from the sensing unit 50d (S430).

As discussed above, the distance between the points P1 and P2 and the duration in which the blood sample pass through the points P1 and P2 can be known, so the controller 120 can obtain the movement speed of the blood sample.

The controller 120 can obtain hematocrit from the movement speed (S440).

Namely, the controller can recognize that hematocrit is a1, a2, and a3 when the speed of the sample is f1, f2, and 13, respectively, with reference to the standard solution table of FIG. 6.

Steps S450 and S460 are the same as described above. Through this method, hematocrit can be obtained on the basis of the movement speed of the blood sample, and a numerical value of cholesterol of the blood sample detected at the reaction unit can be corrected by reflecting the obtained hematocrit.

Figure 12:
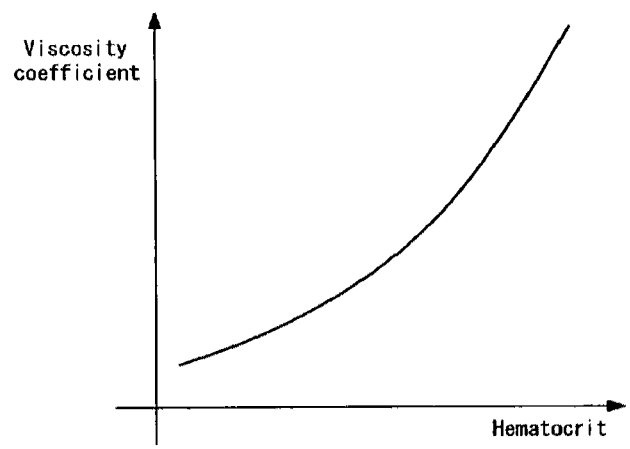
FIG. 12 is a graph showing the relationship between hematocrit and a viscosity coefficient.
Figure 13:
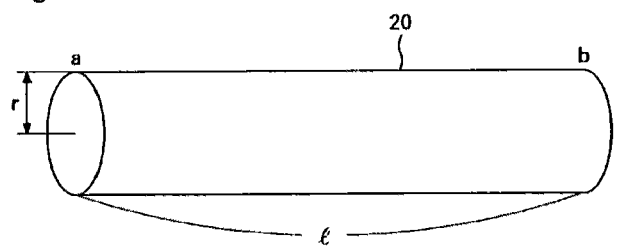
FIG. 13 is a view showing a portion of a channel.

FIG. 12 is a graph showing the relationship between hematocrit and a viscosity coefficient, and FIG. 13 is a view showing a portion of the channel.

An exemplary embodiment of FIGS. 12 and 13 uses a method of using a viscosity coefficient of a blood sample, as an attribute of the blood sample for measuring hematocrit included in the blood sample.

Namely, the relationship between the viscosity coefficient and hematocrit in which when the viscosity coefficient of the blood sample is high, hematocrit is relatively high, and when the viscosity coefficient of the blood sample is low, hematocrit is relatively low is used.

The viscosity coefficient can be obtained by an equation shown below:

$$Q = \frac{\Delta P \pi 4}{8 l \eta}$$

(Q: flow rate, DP: perfusion pressure, r: radius of channel, h: viscosity coefficient, l: distance between two points)

With reference to FIG. 13, the values r and l are known as values related to dimensions of the channel.

Thus, in order to measure viscosity coefficient, a sensing unit 50e (not shown) may be configured to obtain flux of the blood sample in the channel and a pressure difference between points a and b.

For example, the sensing unit 50e may be configured as a flux, pressure difference measurement device using Bernoulli equation.

An operation method according to the exemplary embodiment illustrated in FIGS. 12 and 13 will now be described with reference to FIG. 4.

Steps S410 and S420 are the same as those described above.

The controller 120 can obtain flux and a pressure difference of the blood sample, as an attribute of the blood sample related to hematocrit from the sensing unit 50e (S430).

The controller 120 can obtain viscosity coefficient of the blood sample by using the equation $$Q = \frac{\Delta P \pi 4}{8 l \eta}$$

from the values of flux, pressure difference, radius, and length.

The controller 120 can obtain hematocrit from the viscosity coefficient (S440).

Namely, the controller can recognize that hematocrit is a1, a2, and a3 when the viscosity coefficient of the blood sample is e1, e2, and e3, respectively, with reference to the standard solution table of FIG. 6 illustrating the relationship between the viscosity coefficient and hematocrit.

Steps S450 and S460 are the same as described above. Through this method, hematocrit can be obtained on the basis of the viscosity coefficient of the blood sample, and a numerical value of cholesterol of the blood sample detected at the reaction unit can be corrected by reflecting the obtained hematocrit.

In this manner, the information regarding electric conductivity, light transmittance, contact angle, flux, pressure difference, and speed, the attributes of the blood sample for measuring hematocrit can be measured through the sensing unit 50 of the cartridge 1 as described above.

Accordingly, the reader 100 can correct the cholesterol value measured by the reaction unit 30 on the basis of the attributes of the blood sample, to thus improve the accuracy of the measurement of cholesterol.

Also, it is obvious that the respective sensing units 50 can be configured to collectively and comprehensively measure the attributes of the plurality of blood samples.

The preferred embodiments of the present invention have been described with reference to the accompanying drawings, and it will be apparent to those skilled in the art that various modifications and variations can be made in the present invention without departing from the scope of the invention. Thus, it is intended that any future modifications of the embodiments of the present invention will come within the scope of the appended claims and their equivalents.

INDUSTRIAL APPLICABILITY

According to exemplary embodiments of the present invention, in measuring a particular component included in the sample flowing in the microfluidic sample, a numerical value of hematocrit is reflected, whereby the sample analysis cartridge and sample analysis cartridge reader having an improved accuracy of measurement of the particular component can be provided.

The invention claimed is:
1. A sample analysis cartridge device comprising:
an inlet through which a blood sample is introduced;
a microfluidic channel connected to the inlet and providing a movement path of the blood sample;
a plurality of branch channels connected to the microfluidic channel at a branch point, one of the plurality of branch channels having a bent portion to equalize a length of paths subsequent to the branch point for the blood sample;

a projection in the microfluidic channel disposed at a location between the inlet and the branch point, and comprising a vent;

a plurality of reaction units respectively formed at the other end of the plurality of branch channels from the branch point and configured to measure a value of a particular component included in the blood sample;

a sensing unit positioned in the projection of the microfluidic channel and configured to sense an attribute of the blood sample; and a controller configured to obtain a hematocrit of the blood sample from the sensed attribute of the blood sample, and compensate the measured value of the particular component based on the obtained hematocrit.

2. The device of claim 1, wherein the controller is configured to obtain the hematocrit by comparing the attribute of the blood sample sensed in the sensing unit with a predetermined table.

3. The device of claim 1, wherein the attribute of the blood sample comprises at least one of electric conductivity of the blood sample, light transmittance of the blood sample, a contact angle between the blood sample and an inner wall of the microfluidic channel, a flux of the blood sample per second, a pressure difference between two points of the blood sample, and a duration in which the blood sample passes through two points in the microfluidic channel.

4. The device of claim 1, wherein the microfluidic channel is branched into a plurality of child channels to provide movement paths to the plurality of reaction units, and the microfluidic channel comprises a projection having a predetermined length, before being branched into the plurality of child channels, the projection comprising a vent formed on one end, and wherein the sensing unit comprises a plurality of electrodes positioned in the projection to sense electric conductivity of the blood sample.

5. The device of claim 1, wherein the sensing unit comprises a light emitting unit emitting light at a certain angle to a movement direction of the blood sample and a light receiving unit receiving the light emitted from the light emitting unit and passed through the microfluidic channel, in order to sense a light transmittance of the blood sample or a contact angle between the blood sample and an inner wall of the microfluidic channel.

6. The device of claim 5, wherein the light emitting unit is configured as at least one of a light emitting diode, a lamp, and a laser, and wherein the light receiving unit for sensing the light transmittance is configured as at least one of a photo diode, a charge coupled device array, and a photo diode array, and the light receiving unit for sensing the contact angle is configured as at least one of a charge coupled device array and a photo diode array.

7. The device of claim 3, wherein the sensing unit is further configured to sense the flux and the pressure difference.

8. The device of claim 1, wherein the sensing unit comprises a first sensing unit for sensing whether or not the blood sample has passed a first designated position of the microfluidic channel and a second sensing unit for sensing whether or not the blood sample has passed a second designated position of the microfluidic channel.

9. The device of claim 1, wherein the particular component includes at least one of glycolysis or cholesterol.

10. The device of claim 3, wherein the hematocrit is obtained by:

obtaining a value of the attribute of the blood sample, and correlating the value of the attribute of the blood sample with a corresponding hematocrit in a predetermined standard solution table.

* * * * *